United States Patent [19]

Törnblom

[11] Patent Number: 4,789,828
[45] Date of Patent: Dec. 6, 1988

[54] COOLANT STRUCTURE FOR A DEVICE FOR DETERMINING THE QUALITY OF HOT TEST OBJECTS

[75] Inventor: Bengt H. Törnblom, Västerås, Sweden

[73] Assignee: Tornbloms Kvalitetskontroll AB, Sweden

[21] Appl. No.: 37,683

[22] Filed: Apr. 13, 1987

[30] Foreign Application Priority Data

Apr. 16, 1986 [SE] Sweden ............................... 8601723

[51] Int. Cl.$^4$ ...................... G01N 27/72; G01R 33/12
[52] U.S. Cl. .................................... 324/224; 324/238; 324/262
[58] Field of Search ............... 324/224, 225, 239–243, 324/262; 336/57; 165/47

[56] References Cited

U.S. PATENT DOCUMENTS 3,497,799   2/1970  Harmon ............................... 324/237
4,027,233   5/1977  Shmakov et al. .................... 324/224

Primary Examiner—Reinhard J. Eisenzopf
Assistant Examiner—Walter E. Snow
Attorney, Agent, or Firm—Watson, Cole, Grindle & Watson

[57] ABSTRACT

A device for quality testing hot test objects, comprises at least one coolant-cooled rotatable body, and at least one transducer (for example a surface transducer coil) eccentrically mounted in or on the body to move along an endless path in close proximity to a surface of the test object. The transducer is conncted directly or indirectly to an associated sensing circuit. A device according to the invention is characterized in that the flow of coolant is adapted to take place via an inlet channel and an outlet channel, both of which are disposed close to the axis of rotation of the body, and at least one further channel extending between the inlet and outlet channel to convey coolant at least close to the transducer(s).

7 Claims, 1 Drawing Sheet

COOLANT STRUCTURE FOR A DEVICE FOR DETERMINING THE QUALITY OF HOT TEST OBJECTS

TECHNICAL FIELD

This invention relates to a device for testing and/or measurement of hot objects (hereinafter referred to as "test objects"), comprising at least one rotating body cooled by means of a coolant, and at least one transducer eccentrically mounted in or on the body, for example a surface transducer coil, arranged to move along a circular or similar closed path across or adjacent to a surface of the test object. The transducer is intended to be connected directly or indirectly, for example via slip rings or an inductive rotary signal transmission, to an associated measuring and/or control device.

To transmit signals between a movable, for example rotary, transducer and a more stationary electronic measuring equipment, slip rings are normally used. However, these are fragile and unstable in their function, and any failure in signal transmission is likely to result in deteriorated measurement properties.

DISCUSSION OF PRIOR ART

U.S. patent application Ser. No. 816,270 filed on Jan. 6, 1986 in the name of Törnblom and issued Mar. 29, 1988 as U.S. Pat. No. 4,734,642 a device which solves the above-mentioned problems. However, the disadvantages of this device are, on the one hand, that its speed of rotation is limited because of the relatively large mechanical mass of the pendulum used therein and, on the other hand, its relatively large overall height which, for example in the case of billets testing, may be inconvenient because of the limited space available between strands of the billets.

A solution to the problems just mentioned is the object of published Swedish Patent Application No. 8503894-1. This application describes a device which is useful in, for example, eddy current testing, including the use of several carrier frequencies at the same time as, for example, in vector transformation. A device as described in this Swedish application is designed for the testing and/or measurement of test objects, for example hot continuously cast billets with respect to at least one quality parameter for example the presence of surface cracks on the test object, the inclusion of a gas bubble or an occlusion of a foreign body.

The device described in the Swedish application includes at least one transducer, for example a surface transducer coil, a stator, a rotor, a signal transmission and a drive means, for example a V-belt engaging the rotor, to rotate the rotor. This device is characterized in that it is at least partially based on utilizing eddy current techniques. The movement of the transducer in relation to the test object can be considered to be composed of at least two movements of different velocities and movement patterns which are superimposed on one another. The at least one transducer is eccentrically located in or on the rotor and is able to move in a plane substantially parallel to a part of the test object and signal transmission means is provided in the form of at least one stator winding and at least one rotor winding which rotates with the rotor relative to the stator winding, the at least one transducer being directly or indirectly connected to the rotor winding.

One problem in connection with use of the above-described device is the efficiency of cooling. In this known device a liquid coolant is allowed to pass into the rotor through a channel or a tube extending in the direction of the axis of rotation of the rotor and from there out towards the at least one transducer, which is cooled by the coolant. The coolant is thrown out from the periphery of the rotor by means of the centrifugal force. The consequence of this is that it is difficult to provide a closed coolant flow, which in turn may result in the device becoming orientation sensitive, since for example, it may be difficult to operate the transducer/device upside down for scanning the underside of the billet.

In certain situations this can be a problem, and a device according to the present invention aims to provide a solution to the problem mentioned above and other problems associated therewith.

SUMMARY OF THE INVENTION

According to the invention a device for determining the quality of a hot test object which device comprises a body mounted for rotation about an axis and at least one transducer, eccentrically mounted on the body and thus adapted to move along a closed path adjacent to a surface of the test object and an associated sensing means is characterized in that the coolant flow is adapted to take place in one direction via a tube or a channel, opening out into or in close proximity to the center of the body, and in the opposite direction via a channel or a tube which completely or partially surrounds the first-mentioned tube/channel and is connected to the first-mentioned tube/channel in a closed circuit through cooling channels/tubes in the body. This arrangement provides a completely closed flow and no problems arise with liquid coolant close to or on the test object. In the case of, for example, crack detection on hot continuously cast billets, it is often required that the transducer performs a very fine-meshed scanning of the billet surface in order to find and detect all cracks. To accomplish this it is advantageous, for example, to rotate an eddy current transducer at a relatively high velocity. A problem in this connection is to be able to cool the body and the at least one transducer it supports in a simple and efficient way. This problem is solved by means of the invention.

The above-mentioned prior art problems caused by liquid coolant (e.g. water) being thrown out from the rotating body by means of the centrifugal force are thus avoided. In prior art arrangements of this kind it has often been necessary to capture the discharged coolant while at the same time limits have been set on the orientations of the device which can be used in practice. In the present application, both the coolant inlet and the coolant outlet are arranged close to the rotational axis of the body which entails large practical advantages, for example in that the device can be used in any orientation and in that no surrounding coolant capturing means is required. An unexpected consequence of the invention is that the dimensions of the device can be kept small.

The combination of a device of small dimensions and low weight also makes a device according to this invention well suited to being rapidly moved across the surface of a test object by means of a manipulator, for example an industrial robot. This makes it possible to scan a relatively large billet surface per unit of time with a single device.

The device according to this invention can be considered to be an improvement of the devices disclosed in the above-mentioned U.S. pat. application Ser. No. 816,270 now U.S. Pat. No. 4,734,649 and published Swedish Application No. 8503894-1.

BRIEF DESCRIPTION OF THE DRAWINGS

The invention will now be further described, by way of example, with reference to the accompanying drawing, in which.

DESCRIPTION OF PREFERRED EMBODIMENT

Figure 1:
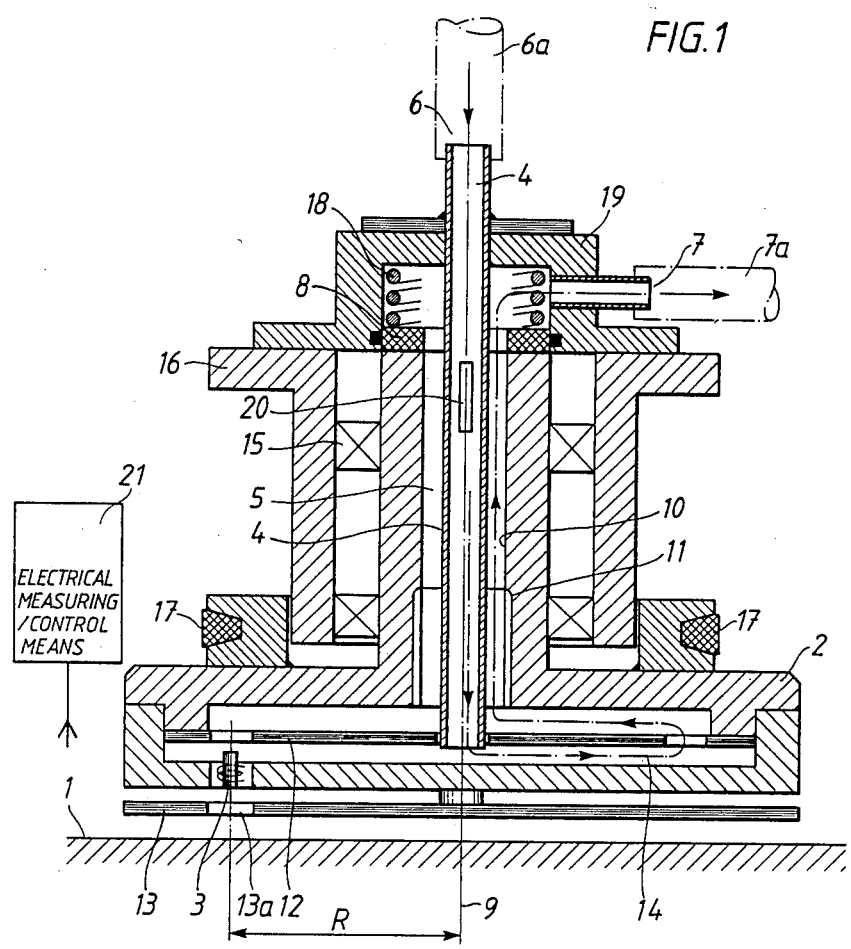
FIG. 1 is a sectional side elevation of a crack-sensing device in accordance with the invention, and FIG. 2 schematically indicates the form of scan trace by which a test object is tested with the device of FIG. 1.

The device illustrated in FIG. 1 is adapted to detect cracks on, for example, a surface of a hot continuously cast billet 1. As mentioned above, it is often required that the crack testing device should perform a very fine-meshed scanning of the surface of the billet 1 in order to find and detect all the cracks that exist. The device comprises a rotatable body 2 rotating about an axis 9 and a transducer 3 mounted eccentrically in or on the body 2. The body 2 has a shaft-like portion 10 and a channel 5 extending along the axis of rotation, a tube 4 for liquid coolant being inserted into the channel 5 and opening out into the body 2. At the lower end of the tube 4, channels 14 are provided in the body 2, which channels 14 communicate with that part of the channel 5 surrounding the tube 4, or (not shown) with another tube or separate channel. Coolant is adapted to be introduced from an inlet connection 4a into the tube 4 via its end 6, to pass through the body 2 via the channels 14, to be transported back to flow up around the tube 4 and to be discharged at a point 7 into an outlet connection 7a. However, coolant flow in the opposite direction could just as well be employed. In close proximity to the coolant channels 14 in the body 2 there is arranged at least one transducer 3 which, of course, is provided with associated measuring and/or control means and which is completely or partially based on the use of eddy current techniques. Coolant is intended to be transported past and even through the transducer 3 in order to cool it and its environment. The channels 14 in the body 2 are provided with partition walls 12 for controlling and/or distributing the coolant flow and optionally also for increasing the number of channels. Fixed, non-rotation connections for coolant are arranged on the inner tube 4, at the end 6, and at the point 7. A coolant seal packing is shown at 8 arranged around the axis of revolution 9 of the body 2. The walls of the cooling channel in the shaft-like portion 10 are, at 11, provided with threads or similar projections arranged to facilitate the flow of the coolant. A heat shield 13 for the body 2, serves as protection against heat radiation from the test object 1 and has a window 13a through which the transducer 3 can "view" the test object. Bearings 15 are provided for supporting body 2, within a flanged support 16 for connection to a suitable base plate or the like (not shown). A V-belt 17 is provided for driving the body 2; however, the driving may be performed in other ways, for example by means gear wheels, screw threads or by the use of a built-in drive motor. A spring 18 is provided for pressing the packing 8 down against the rotating main part of the rotor 2. The illustrated number of tubes placed inside one another in the region of the axis 9 is two, but the number can be increased to three or more.

The device shown in FIG. 1 is suitably provided with a water-cooled casing, which may, for example, be fixed to the base plate.

In certain cases, the test object 1 may consist of an elongated material, for example wire, rod or the like. In this case the test object 1 can then be led to pass through an inner protective tube 20 (only a scrap portion of which is shown) placed inside the inner coolant tube 4. With the test object passing axially through the body 2, the transducer 3 needs to be located in a rotating part of the body 2 which is close to the test object (e.g. in the shaft-like portion 10).

The transducer 3 is most conveniently a coil which generates eddy currents in the test object and monitors for changes in the induced eddy currents caused by surface defects such as cracks, voids or occlusions of foreign matter. For powering the transducer and monitoring its output during use of the device it is possible to use slip rings (e.g. located on the outside of the shaft-like portion 10) which are electrically connected inside the body 2 to the transducer 3 and via sliders, externally of the body 2 to a power supply unit and a sensing or measuring means that gives the required indication of crack detection. Alternatively an external electrical measuring and control means can be inductively coupled to the transducer 3 and this is shown schematically at 21 in FIG. 1.

In certain cases it may also be convenient to locate in the device, for example in the body 2, certain electronic equipment, for example for impedance matching of the transducer 3 to optimise signal transmission to the unit 21.

Figure 2:
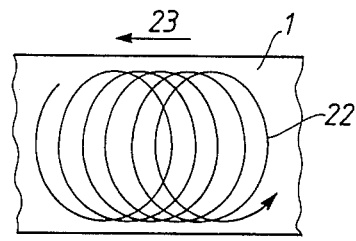

FIG. 2 shows at 22 a typical trace pattern that can be scanned by the transducer 3 as it moves around a closed circular path about the axis 9 as the test object 1 moves in the direction of the arrow 23.

By the term "quality" of a test object is meant, inter alia the extent to which the test object is free of surface cracks, occlusions of foreign bodies or voids; the extent to which the test object meets manufacturing tolerances regarding a dimension of the test object; and the position of the test object relative to a reference position. It will be appreciated, therefore that "quality" is to be construed in a broad manner.

A device according to the foregoing description can be varied in many ways within the scope of the appendant claims.

What is claimed is:

1. A device for determining the quality of a hot test object, comprising a body mounted for rotation about an axis and at least one transducer eccentrically mounted on the body and thus adapted to move along a closed path adjacent to a surface of the test object and an associated sensing means;

a coolant flow within the body takes place via an inlet channel and an outlet channel each adjacent to the axis of rotation of the body and, connecting said channels, at least one further channel which conveys coolant past the vicinity of the at least one transducer; and the coolant flow in one of the inlet and outlet channels flows past a packing seal surrounding the axis of rotation of the body.

2. A device according to claim 1, in which the coolant which flows past the packing seal flows along a channel which rotates with the body.

3. A device according to claim 2, in which the rotating part of the cooling channel is provided with projections to facilitate the flow of coolant.

4. A device according to claim 1, in which there are a plurality of further channels in the body formed by a partition wall perforated in a plurality of locations.

5. A device according to claim 1, in which the body is provided with a heat shield on the side facing the test object, the transducer operating through a window in the shield.

6. A device according to claim 1, in which the inlet and outlet channels are formed by a central cylindrical tube aligned with the axis and a surrounding annular channel.

7. A device for determining the quality of a hot test object, comprising:
 a body mounted for rotation about an axis;
 at least one transducer eccentrically mounted on the body for movement along a closed path adjacent to a surface of the test object and an associated sensing means; and
 a coolant flow within the body takes place via an inlet channel and an outlet channel each adjacent to the axis of rotation of the body, said outlet channel at least partially surrounding said inlet channel and connected thereto in a closed loop via cooling conduits in said body.

* * * * *